United States Patent [19]

Krass

[11] 4,401,602

[45] Aug. 30, 1983

[54] 4-TRIFLUOROMETHYLPHENOXY-BENZALDOXIMES

[75] Inventor: Dennis K. Krass, Canal Fulton, Ohio

[73] Assignee: PPG Industries, Inc., Pittsburgh, Pa.

[21] Appl. No.: 373,780

[22] Filed: Apr. 30, 1982

Related U.S. Application Data

[60] Division of Ser. No. 136,171, Apr. 15, 1980, Pat. No. 4,344,789, which is a continuation-in-part of Ser. No. 38,043, May 11, 1979, abandoned.

[51] Int. Cl.³ .................. C07C 121/80; C07C 131/00
[52] U.S. Cl. ................................ 260/465 E; 564/265
[58] Field of Search ..................... 260/465 E; 564/265

[56] References Cited

FOREIGN PATENT DOCUMENTS 52-46286 11/1977 Japan.

Primary Examiner—Dolph H. Torrence
Attorney, Agent, or Firm—Edward J. Whitfield

[57] ABSTRACT

Compounds, such as 5-(2-chloro-4-trifluoromethylphenoxy)-2-nitroacetophenone oxime-O-(acetic acid, methyl ester) and 5-(2-chloro-4-trifluoromethylphenoxy)-2-chloroacetophenone oxime-O-(acetic acid, methyl ester), are useful for postemergence and preemergence control of weeds, and are represented by Formula I of the application.

1 Claim, No Drawings

4-TRIFLUOROMETHYLPHENOXY-BENZALDOXIMES

RELATED APPLICATIONS

This is a division of application Ser. No. 136,171, filed Apr. 15, 1980, now U.S. Pat. No. 4,344,789, which application is a continuation-in-part of application Ser. No. 38,043, filed May 11, 1979, since abandoned.

BACKGROUND OF THE INVENTION

1. Field of the Invention

The invention pertains to compounds as defined by the graphic Formula I, mentioned herein, such as 5-(2-chloro-4-trifluoromethylphenoxy)-2-nitroacetophenone-O-(acetic acid, methyl ester), their use to control weeds, and the useful intermediates as defined by graphic Formulas II and III, mentioned herein.

2. Summary of the Invention

The invention concerns useful compounds graphically represented by Formula I, mentioned herein; the useful aldehydes, ketones, and oximes of the compounds graphically represented by Formula II and Formula III, mentioned herein; the method of preparing the compounds; and the method of controlling the weeds described herein with the compounds. For example, 5-(2-chloro-4-trifluoromethylphenoxy)-2-nitroacetophenone oxime-O-(acetic acid, methyl ester) or 5-(2-chloro-4-trifluoromethylphenoxy)-2-chlorobenzaldoxime-O-(2-propionic acid, methyl ester) are useful for controlling weeds described herein.

DETAILED DESCRIPTION OF THE INVENTION

The novel, agriculturally useful compounds in both their anti and syn forms are graphically represented by Formula I:

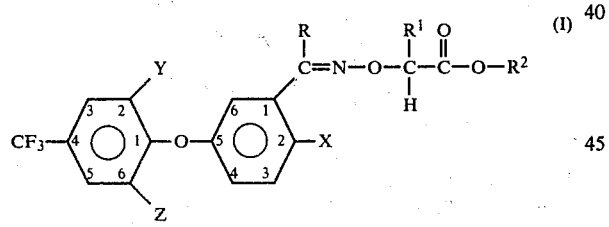

wherein Y is hydrogen or chlorine; Z is chlorine when Y is chlorine, or Z is hydrogen when Y is chlorine or hydrogen; X is nitro (—NO$_2$), a halogen, preferably chloro (Cl—), or cyano (—CN); R is hydrogen or an alkyl of up to three carbon atoms, preferably methyl (—CH$_3$); R$^1$ is hydrogen or methyl (—CH$_3$); and R$^2$ is hydrogen, an alkyl of up to ten carbon atoms, preferably an alkyl of up to four carbon atoms (methyl is especially preferred); or an agronomically soluble salt ion, e.g. a metal ion such as sodium, potassium, lithium, or ammonium (NH$_4$+), or a mono-, di-, or trialkyl substituted ammonium ion such as trimethylammonium or monoethanol ammonium ion; preferred are sodium, potassium, and ammonium.

Some examples of compounds of Formula I are:

I. R is an alkyl of up to three carbon atoms;
  a. X is a halogen; and Y, Z, R$^1$, and R$^2$ are as defined.
    ammonium 5-(2-chloro-4-trifluoromethylphenoxy)-2-chloropropiophenone oxime-O-acetate,
    5-(2-chloro-4-trifluoromethylphenoxy)-2-iodo-2'-methylpropiophenone oxime-O-(2-propionic acid, butyl ester),
    5-(4-trifluoromethylphenoxy)-2-fluorobutyrophenone oxime-O-(2-propionic acid, decyl ester),
    sodium 5-(2,6-dichloro-4-trifluoromethylphenoxy)-2-bromopropiophenone oxime-O-acetate,
    5-(2,6-dichloro-4-trifluoromethylphenoxy)-2-chloropropiophenone oxime-O-(2-propionic acid, 1,1-dimethyl ethyl ester),
    5-(4-trifluoromethylphenoxy)-2-chloro-2-methylpropiophenone oxime-O-(acetic acid, 3,4,5-dimethylheptyl ester).
  b. X is cyano; and Y, Z, R$^1$, and R$^2$ are as defined.
    5-(4-trifluoromethylphenoxy)-2-cyanobutyrophenone oxime-O-(acetic acid, heptyl ester),
    5-(2-chloro-4-trifluoromethylphenoxy)-2-cyanopropiophenone oxime-O-(acetic acid, nonyl ester),
    sodium 5-(2,6-dichloro-4-trifluoromethylphenoxy)-2-cyano-2-methylpropiophenone oxime-O-acetate,
    5-(2-chloro-4-trifluoromethylphenoxy)-2-cyanoacetophenone oxime-O-(2-propionic acid, ethyl ester),
    5-(2-chloro-4-trifluoromethylphenoxy)-2-cyanobutyrophenone oxime-O-(acetic acid, 2-ethylhexyl ester).
  c. X is nitro; and Y, Z, R$^1$, and R$^2$ are as defined.
    5-(2,6-dichloro-4-trifluoromethylphenoxy)-2-nitrobutyrophenone oxime-O-(2-propionic acid, propyl ester),
    5-(4-trifluoromethylphenoxy)-2-nitrobutyrophenone oxime-O-(2-propionic acid, butyl ester),
    methylammonium 5-(2-chloro-4-trifluoromethylphenoxy)-2-nitro-2'-methylpropiophenone oxime-O-acetate,
    5-(2,6-dichloro-4-trifluoromethylphenoxy)-2-nitrobutyrophenone oxime-O-(2-propionic acid, 1,1-dimethylpropyl ester),
    5-(2-chloro-4-trifluoromethylphenoxy)-2-nitropropiophenone oxime-O-(acetic acid, pentanyl ester),
    5-(2-chloro-4-trifluoromethylphenoxy)-2-nitropropiophenone oxime-O-(2-propionic acid, decyl ester),
    5-(2,6-dichloro-4-trifluoromethylphenoxy)-2-nitroacetophenone oxime-O-(acetic acid, isobutyl ester),
    5-(2-chloro-4-trifluoromethylphenoxy)-2-nitroacetophenone oxime-O-(acetic acid, isopropyl ester).

II. R is hydrogen;
  a. X is a halogen; and Y, Z, R$^1$, and R$^2$ are as defined.
    dimethylammonium 5-(2-chloro-4-trifluoromethylphenoxy)-2-chlorobenzaldoxime-O-acetate,
    sodium 5-(4-trifluoromethylphenoxy)-2-iodobenzaldoxime-O-acetate,
    5-(2-chloro-4-trifluoromethylphenoxy)-2-fluorobenzaldoxime-O-(2-propanoic acid, 2,3,5-trimethylheptyl),
    5-(2-chloro-4-trifluoromethylphenoxy)-2-chlorobenzaldoxime-O-(2-propanoic acid, methyl ester),
    5-(2,6-dichloro-4-trifluoromethylphenoxy)-2-bromobenzaldoxime-O-(acetic acid, butyl ester),
    5-(4-trifluoromethylphenoxy)-2-fluorobenzaldoxime-O-(acetic acid, pentanyl ester).

b. X is cyano; and Y, Z, $R^1$, and $R^2$ are as defined.
- 5-(2-chloro-4-trifluoromethylphenoxy)-2-cyanobenzaldoxime-O-(acetic acid, 2-methylpropyl ester),
- 5-(2-chloro-4-trifluoromethylphenoxy)-2-cyanobenzaldoxime-O-acetic acid,
- 5-(2-chloro-4-trifluoromethylphenoxy)-2-cyanobenzaldoxime-O-2-propionic acid,
- 5-(2-chloro-4-trifluoromethylphenoxy)-2-cyanobenzaldoxime-O-(2-propionic acid, 1-methylethyl ester),
- sodium 5-(2-chloro-4-trifluoromethylphenoxy)-2-cyanobenzaldoxime-O-(2-propionate),
- 5-(2,6-dichloro-4-trifluoromethylphenoxy)-2-cyanobenzaldoxime-O-(acetic acid, methyl ester),
- trimethylammonium 5-(4-trifluoromethylphenoxy)-2-cyanobenzaldoxime-O-acetate,
- 5-(2-chloro-4-trifluoromethylphenoxy)-2-cyanobenzaldoxime-O-(acetic acid, 3,5-dimethyloctyl ester),
- ammonium 5-(2,6-dichloro-4-trifluoromethylphenoxy)-2-cyanobenzaldoxime-O-(2-propionate),
- 5-(4-trifluoromethylphenoxy)-2-cyanobenzaldoxime-O-acetic acid,
- 5-(2-chloro-4-trifluoromethylphenoxy)-2-cyanobenzaldoxime-O-(2-propionic acid, propyl ester).

c. X is nitro; and Y, Z, $R^1$, and $R^2$ are as defined.
- 5-(4-trifluoromethylphenoxy)-2-nitrobenzaldoxime-O-(acetic acid, 1,1-dimethylethyl ester),
- 5-(2-chloro-4-trifluoromethylphenoxy)-2-nitrobenzaldoxime-O-(2-propionic acid),
- 5-(2,6-dichloro-4-trifluoromethylphenoxy)-2-nitrobenzaldoxime-O-(2-propionic acid, butyl ester),
- 5-(2-chloro-4-trifluoromethylphenoxy)-2-nitrobenzaldoxime-O-(acetic acid, butyl ester),
- 5-(2-chloro-4-trifluoromethylphenoxy)-2-nitrobenzaldoxime-O-(2-propionic acid, 1,1-dimethylethyl ester),
- 5-(2-chloro-4-trifluoromethylphenoxy)-2-nitrobenzaldoxime-O-(acetic acid, nonyl ester),
- 5-(2,6-dichloro-4-trifluoromethylphenoxy)-2-nitrobenzaldoxime-O-(acetic acid, ethyl ester),
- sodium 5-(2-chloro-4-trifluoromethylphenoxy)-2-nitrobenzaldoxime-O-acetate,
- 5-(2-chloro-4-trifluoromethylphenoxy)-2-nitrobenzaldoxime-O-(acetic acid, 2-methylnonyl ester),
- triethylammonium 5-(4-trifluoromethylphenoxy)-2-nitrobenzaldoxime-O-acetate,
- 5-(2-chloro-4-trifluoromethylphenoxy)-2-nitrobenzaldoxime-O-(2-propionic acid),
- 5-(4-trifluoromethylphenoxy)-2-nitrobenzaldoxime-O-(2-propionic acid, heptyl ester).

Novel compounds having useful herbicidal properties and utility as intermediates in the formation of the compounds represented by Formula I are:

A. Compounds Graphically Represented by Formula II

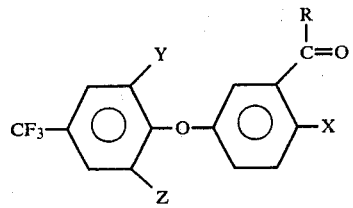

wherein X, Y, Z, and R are as defined herein.
Some examples of general Formula II are:
- 5-(2-chloro-4-trifluoromethylphenoxy)-2-nitrobenzaldehyde,
- 5-(4-trifluoromethylphenoxy)-2-nitrobenzaldehyde,
- 5-(2,6-dichloro-4-trifluoromethylphenoxy)-2-nitrobenzaldehyde,
- 5-(2-chloro-4-trifluoromethylphenoxy)-2-nitroacetophenone,
- 5-(2-chloro-4-trifluoromethylphenoxy)-2-nitropropiophenone,
- 5-(4-trifluoromethylphenoxy)-2-nitroacetophenone,
- 5-(4-trifluoromethylphenoxy)-2-cyanobutyrophenone,
- 5-(2-chloro-4-trifluoromethylphenoxy)-2-bromopropiophenone,
- 5-(2,6-dichloro-4-trifluoromethylphenoxy)-2-fluoroacetophenone,
- 5-(4-trifluoromethylphenoxy)-2-nitro-2'-methylpropiophenone,
- 5-(2-chloro-4-trifluoromethylphenoxy)-2-chlorobenzaldehyde,
- 5-(2-chloro-4-trifluoromethylphenoxy)-2-cyanobenzaldehyde,
- 5-(4-trifluoromethylphenoxy)-2-chloropropiophenone.

B. Compounds Graphically Represented by Formula III

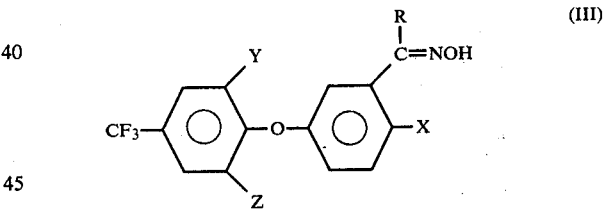

wherein X, Y, Z, and R are as defined herein:
Some examples of general Formula III are:
- 5-(2-chloro-4-trifluoromethylphenoxy)-2-nitrobenzaldoxime,
- 5-(4-trifluoromethylphenoxy)-2-nitrobenzaldoxime,
- 5-(2,6-dichloro-4-trifluoromethylphenoxy)-2-nitrobenzaldoxime,
- 5-(2-chloro-4-trifluoromethylphenoxy)-2-nitroacetophenone oxime,
- 5-(4-trifluoromethylphenoxy)-2-nitroacetophenone oxime,
- 5-(2-chloro-4-trifluoromethylphenoxy)-2-nitrobutyrophenone oxime,
- 5-(2,6-dichloro-4-trifluoromethylphenoxy)-2-nitropropiophenone oxime,
- 5-(4-trifluoromethylphenoxy)-2-cyanobutyrophenone oxime,
- 5-(2,6-dichloro-4-trifluoromethylphenoxy)-2-nitro-2'-methylpropiophenone oxime,
- 5-(2-chloro-4-trifluoromethyl-6-fluorophenoxy)-2-fluorobenzaldoxime.

As used herein and in the claims, the word "compound" and the name of the compound, for example 5-(2-chloro-4-trifluorophenoxy)-2-nitroacetophenone oxime-O-(acetic acid, methyl ester) refers to syn and anti isomers of the compound, as well as to other stereo isomers of the compounds.

Although all of the compounds as disclosed herein are useful for the purposes disclosed herein, some compounds are preferred over others. In the compounds described herein, Z is preferably hydrogen; X is preferably a cyano, more preferably chloro (Cl), but especially nitro ($NO_2$); Y is preferably chloro (—Cl); R is preferably hydrogen or methyl ($CH_3$); and $R^2$ is preferably an alkyl of up to four carbon atoms, especially methyl ($CH_3$) or hydrogen, but also preferred are the agronomically useful salt ions mentioned herein, particularly sodium ($NA^+$), potassium ($K^+$), and ammonium ($NH^+_4$).

A very useful group of compounds graphically represented by Formula I and a very useful group of aldehydes, ketones, and oximes graphically represented by Formulas II and III are those of Formulas IV, V, and VI:

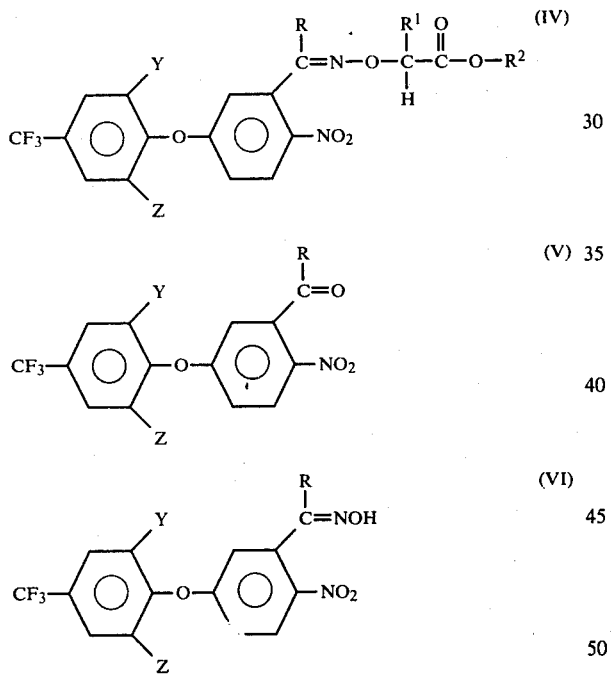

in which Y, Z, R, $R^1$, and $R^2$ are as defined.

A. Representative examples of these very useful compounds of Formula IV are those in which:

I. R is an alkyl of up to three carbon atoms, and
   a. $R^1$ is methyl, such as:
      5-(4-trifluoromethylphenoxy)-2-nitrobutyrophenone oxime-O-(2-propionic acid, methyl ester),
      5-(2-chloro-4-trifluoromethylphenoxy)-2-nitro-2'-methylpropiophenone oxime-O-(2-propionic acid, butyl ester),
      5-(2,6-dichloro-4-trifluoromethylphenoxy)-2-nitrobutyrophenone oxime-O-(2-propionic acid, 1,1-dimethylethyl ester),
      5-(4-trifluoromethylphenoxy)-2-nitropropiophenone oxime-O-(2-propionic acid, 1-methylpropyl ester),
      5-(2-chloro-4-trifluoromethylphenoxy)-2-nitropropiophenone oxime-(2-propionic acid, methylethyl ester),
      5-(2,6-dichloro-4-trifluoromethylphenoxy)-2-nitroacetophenone oxime-O-(2-propionic acid, propyl ester),
      5-(2-chloro-4-trifluoromethylphenoxy)-2-nitroacetophenone oxime-O-(2-propionic acid, ethyl ester),
      5-(2,6-dichloro-4-trifluoromethylphenoxy)-2-nitroacetophenone oxime-O-(2-propionic acid).
   b. $R^1$ is hydrogen, such as:
      5-(2-chloro-4-trifluoromethylphenoxy)-2-nitro-2'-methylpropiophenone oxime-O-(acetic acid, 1,1-dimethyl ester),
      5-(4-trifluoromethylphenoxy)-2-nitrobutyrophenone oxime-O-(acetic acid, 1-methylpropyl ester),
      5-(2,6-dichloro-4-trifluoromethylphenoxy)-2-nitrobutyrophenone oxime-O-(acetic acid, 2-methylpropyl ester),
      5-(2-chloro-4-trifluoromethylphenoxy)-2-nitropropiophenone oxime-O-(acetic acid, butyl ester),
      5-(4-trifluoromethylphenoxy)-2-nitropropiophenone oxime-O-(acetic acid, propyl ester),
      5-(2,6-dichloro-4-trifluoromethylphenoxy)-2-nitroacetophenone oxime-O-(acetic acid, methylethyl ester),
      5-(2-chloro-4-trifluoromethylphenoxy)-2-nitroacetophenone oxime-O-acetic acid,
      5-(2,6-dichloro-4-trifluoromethylphenoxy)-2-nitro-2'-methylpropiophenone oxime-O-acetic acid.

II. R is hydrogen, and
   a. $R^1$ is methyl, such as:
      5-(4-trifluoromethylphenoxy)-2-nitrobenzaldoxime-O-(2-propionic acid, 1,1-dimethylethyl ester),
      5-(2-chloro-4-trifluoromethylphenoxy)-2-nitrobenzaldoxime-O-(2-propionic acid, methylethyl ester),
      5-(2,6-dichloro-4-trifluoromethylphenoxy)-2-nitrobenzaldoxime-O-(2-propionic acid, butyl ester),
      5-(4-trifluoromethylphenoxy)-2-nitrobenzaldoxime-O-(2-propionic acid).
   b. $R^1$ is hydrogen, such as:
      5-(4-trifluoromethylphenoxy)-2-nitrobenzaldoxime-O-(acetic acid, 1,1-dimethylethyl ester),
      5-(2-chloro-4-trifluoromethylphenoxy)-2-nitrobenzaldoxime-O-(acetic acid, 2-methylpropyl ester),
      5-(2,6-dichloro-4-trifluoromethylphenoxy)-2-nitrobenzaldoxime-O-(acetic acid, ethyl ester),
      5-(2-chloro-4-trifluoromethylphenoxy)-2-nitrobenzaldoxime-O-acetic acid.

B. Examples of very useful ketones and aldehydes represented by Formula V are those in which:

I. R is hydrogen, such as:
   5-(2-chloro-4-trifluoromethylphenoxy)-2-nitrobenzaldehyde,
   5-(4-trifluoromethylphenoxy)-2-nitrobenzaldehyde,
   5-(2,6-dichloro-4-trifluoromethylphenoxy)-2-nitrobenzaldehyde.

II. R is an alkyl of up to three carbon atoms, such as:
   5-(2-chloro-4-trifluoromethylphenoxy)-2-nitroacetophenone,
   5-(2-chloro-4-trifluoromethylphenoxy)-2-nitropropiophenone, 5-(4-trifluoromethylphenoxy)-2-nitroacetophenone.

C. Examples of very useful oximes graphically represented by Formula VI are those in which:

I. R is hydrogen, such as:
5-(2-chloro-4-trifluoromethylphenoxy)-2-nitrobenzaldoxime,
5-(4-trifluoromethylphenoxy)-2-nitrobenzaldoxime,
5-(2,6-dichloro-4-trifluoromethylphenoxy)-2-nitrobenzaldoxime.

II. R is an alkyl of up to three carbon atoms, such as:
5-(2-chloro-4-trifluoromethylphenoxy)-2-nitroacetophenone oxime,
5-(4-trifluoromethylphenoxy)-2-nitroacetophenone oxime,
5-(2-chloro-4-trifluoromethylphenoxy)-2-nitrobutyrophenone oxime,
5-(2,6-dichloro-4-trifluoromethylphenoxy)-2-nitropropiophenone oxime.

Preferred compounds represented by Formula I are:
5-(2-chloro-4-trifluoromethylphenoxy)-2-nitroacetophenone oxime-O-(acetic acid, ethyl ester),
5-(2-chloro-4-trifluoromethylphenoxy)-2-nitroacetophenone oxime-O-(2-propionic acid, methyl ester),
5-(2-chloro-4-trifluoromethylphenoxy)-2-nitroacetophenone oxime-O-(2-propionic acid, ethyl ester),
5-(2-chloro-4-trifluoromethylphenoxy)-2-nitroacetophenone oxime-O-(acetic acid, methyl ester),
5-(2-chloro-4-trifluoromethylphenoxy)-2-nitrobenzaldoxime-O-(acetic acid, methyl ester),
5-(2-chloro-4-trifluoromethylphenoxy)-2-nitrobenzaldoxime-O-acetic acid,
sodium 5-(2-chloro-4-trifluoromethylphenoxy)-2-nitrobenzaldoxime-O-acetate,
5-(2-chloro-4-trifluoromethylphenoxy)-2-nitroacetophenone oxime-O-acetic acid,
potassium 5-(2-chloro-4-trifluoromethylphenoxy)-2-nitroacetophenone oxime-O-acetate,
5-(2-chloro-4-trifluoromethylphenoxy)-2-nitroacetophenone oxime-O-(2-propionic acid).

The ammonium, sodium, and potassium salts of the above-mentioned acetic and 2-propionic acids:
5-(2-chloro-4-trifluoromethylphenoxy)-2-chloroacetophenone oxime-O-(acetic acid, ethyl ester),
5-(2-chloro-4-trifluoromethylphenoxy)-2-chloroacetophenone oxime-O-(2-propionic acid, methyl ester),
5-(2-chloro-4-trifluoromethylphenoxy)-2-chloroacetophenone oxime-O-(2-propionic acid, ethyl ester),
(2-chloro-4-trifluoromethylphenoxy)-2-chloroacetophenone oxime-O-(acetic acid, methyl ester),
5-(2-chloro-4-trifluoromethylphenoxy)-2-chlorobenzaldoxime-O-(2-propionic acid,
5-(2-chloro-4-trifluoromethylphenoxy)-2-chlorobenzaldoxime-O-acetic acid,
5-(2-chloro-4-trifluoromethylphenoxy)-2-chlorobenzaldoxime-O-(2-propionic acid, methyl ester),
5-(2-chloro-4-trifluoromethylphenoxy)-2-chlorobenzaldoxime-O-(acetic acid, methyl ester).

The ammonium, sodium, and potassium salts of the above-mentioned acetic and 2-propionic acids:
5-(2-chloro-4-trifluoromethylphenoxy)-2-cyanoacetophenone oxime-O-(acetic acid, ethyl ester),
5-(2-chloro-4-trifluoromethylphenoxy)-2-cyanoacetophenone oxime-O-(2-propionic acid, methyl ester),
5-(2-chloro-4-trifluoromethylphenoxy)-2-cyanoacetophenone oxime-O-(2-propionic acid, ethyl ester),
5-(2-chloro-4-trifluoromethylphenoxy)-2-cyanoacetophenone oxime-O-(acetic acid, methyl ester),
5-(2-chloro-4-trifluoromethylphenoxy)-2-cyanobenzaldoxime-O-(acetic acid, methyl ester),
5-(2-chloro-4-trifluoromethylphenoxy)-2-cyanobenzaldoxime-O-acetic acid,
sodium 5-(2-chloro-4-trifluoromethylphenoxy)-2-cyanobenzaldoxime-O-acetate,
5-(2-chloro-4-trifluoromethylphenoxy)-2-cyanoacetophenone oxime-O-acetic acid,
potassium 5-(2-chloro-4-trifluoromethylphenoxy)-2-cyanoacetophenone oxime-O-acetic acid,
5-(2-chloro-4-trifluoromethylphenoxy)-2-cyanoacetophenone oxime-O-(2-propionic acid).

Very preferred compounds in order of increasing preference are:

The sodium, potassium, and ammonium salts of:
5-(2-chloro-4-trifluoromethylphenoxy)-2-cyanobenzaldoxime-O-(2-propionic and acetic acids),
5-(2-chloro-4-trifluoromethylphenoxy)-2-cyanoacetophenone oxime-O-(2-propionic and acetic acids),
5-(2-chloro-4-trifluoromethylphenoxy)-2-chlorobenzaldoxime-O-(2-propionic and acetic acids),
5-(2-chloro-4-trifluoromethylphenoxy)-2-chloracetophenone oxime-O-(2-propionic and acetic acids), The compounds of:
5-(2-chloro-4-trifluoromethylphenoxy)-2-cyanobenzaldoxime-O-(2-propionic acid),
5-(2-chloro-4-trifluoromethylphenoxy)-2-cyanobenzaldoxime-O-acetic acid,
5-(2-chloro-4-trifluoromethylphenoxy)-2-cyanobenzaldoxime-O-(2-propionic, methyl ester),
5-(2-chloro-4-trifluoromethylphenoxy)-2-cyanobenzaldoxime-O-(acetic acid, methyl ester),
5-(2-chloro-4-trifluoromethylphenoxy)-2-cyanoacetophenone oxime-O-(2-propionic acid),
5-(2-chloro-4-trifluoromethylphenoxy)-2-cyanoacetophenone oxime-O-acetic acid,
5-(2-chloro-4-trifluoromethylphenoxy)-2-cyanoacetophenone oxime-O-(2-propionic acid, methyl ester),
5-(2-chloro-4-trifluoromethylphenoxy)-2-cyanoacetophenone oxime-O-(acetic acid, methyl ester),
5-(2-chloro-4-trifluoromethylphenoxy)-2-chlorobenzaldoxime-O-(2-propionic acid),
5-(2-chloro-4-trifluoromethylphenoxy)-2-chlorobenzaldoxime-O-acetic acid,
5-(2-chloro-4-trifluoromethylphenoxy)-2-chlorobenzaldoxime-O-(2-propionic acid, methyl ester),
5-(2-chloro-4-trifluoromethylphenoxy)-2-chlorobenzaldoxime-O-(acetic acid, methyl ester),
5-(2-chloro-4-trifluoromethylphenoxy)-2-chloroacetophenone oxime-O-(2-propionic acid),
5-(2-chloro-4-trifluoromethylphenoxy)-2-chloroacetophenone oxime-O-acetic acid, 5-(2-chloro-4-trifluoromethylphenoxy)-2-chloroacetophenone oxime-O-(2-propionic, methyl ester), 5-(2-chloro-4-trifluoromethylphenoxy)-2-chloroacetophenone oxime-O-(acetic acid, methyl ester), 5-(2-chloro-4-trifluoromethylphenoxy)-2-nitrobenzaldoxime-O-(2-propionic and acetic acids), 5-(2-chloro-4-trifluoromethylphenoxy)-2-nitroacetophenone oxime-O-(2-propionic and acetic acids), 5-(2-chloro-4-trifluoromethylphenoxy)-2-nitrobenzaldoxime-O-(2-propionic acid), 5-(2-chloro-4-trifluoromethylphenoxy)-2-nitrobenzaldoxime-O-acetic acid, 5-(2-chloro-4-trifluoromethylphenoxy)-2-nitrobenzaldoxime-O-(2-propionic acid, methyl ester), 5-(2-chloro-4-trifluoromethylphenoxy)-2-nitrobenzaldoxime-O-(acetic acid, methyl ester).

5-(2-chloro-4-trifluoromethylphenoxy)-2-nitroacetophenone oxime-O-(2-propionic acid), 5-(2-chloro-4-trifluoromethylphenoxy)-2-nitroacetophenone oxime-O-acetic acid, 5-(2-chloro-4-trifluoromethylphenoxy)-2-nitroacetophenone oxime-O-(2-propionic acid, methyl ester), 5-(2-chloro-4-trifluoromethylphenoxy)-2-nitroacetophenone oxime-O-(acetic acid, methyl ester), The most preferred compound is 5-(2-chloro-4-trifluoromethylphenoxy)-2-nitroacetophenone oxime-O-(acetic acid, methyl ester).

SYNTHESIS

A. General Procedure

Although the synthesis of the compounds described herein can be performed by any of the procedures known to those skilled in the art, one appropriate synthesis for the compounds described herein is described herein and illustrated by the synthesis examples.

a. Formation of the Carboxy Compounds

1. Formation of the ketone and aldehyde compounds other than the 2-cyano substituted compounds The appropriately substituted p-chlorobenzotrifluoride is reacted with an appropriately substituted salt of a metal-3-substituted carbonyl phenoxide or its ketal or acetal or a cation of sodium (Na+) or potassium (K+), preferably K+, to form a compound of Formula II, where X is hydrogen, which is then halogenated or nitrated by standard methods to form a compound of Formula II, which is separated from the reaction mixture.

2. Formation of the 2-cyano substituted ketone and aldehyde compounds

The compounds of general Formula I (where X=cyano) may be prepared by reduction of the carbonyl compound (or its acetal or ketal) of general Formula II (where X=nitro) to the amino compound (X=NH$_2$) followed by diazotization and treatment with CuCN, affording the cyanocarbonyl compound (general Formula II where X=cyano). Subsequent conversion to the oxime (Formula III where X=cyano) and carboxy oximes (Formula I where X=cyano) can be accomplished by methods described herein.

b. Formation of Oximes

1. Procedure When R is Hydrogen

When R is hydrogen, the appropriate aldehyde represented by Formula II wherein R is hydrogen; for example (0.001 mole) is dissolved in 20 milliliters of tetrahydrofuran (THF) and 12 milliliters of absolute ethanol. To this stirred solution is added hydroxylamine hydrochloride (0.012 mole) in 1 milliliter of water, and then 0.6 grams (0.015 mole) sodium hydroxide in 5 milliliters of water. The solution is stirred overnight at ambient temperature and the tetrahydrofuran and ethanol are stripped off in vacuo, leaving a two-phase system. The oil phase is dissolved in chloroform (HCCL$_3$) and then separated from the aqueous phase. The chloroform layer is then extracted with water, and with a saturated sodium chloride solution, and then dried over anhydrous magnesium sulfate (MgSO$_4$). Filtration and evaporation affords the crude product of the oximes of Formula III wherein R is hydrogen. The crude product can be recrystallized in carbon tetrachloride (CCl$_4$).

2. Procedure When R is an Alkyl of up to Three Carbon Atoms

An alternate procedure is used when R in Formula II is an alkyl described herein. This procedure employs anhydrous conditions. For example (0.0056 mole) of the appropriate carbonyl compound of Formula II, wherein R is an alkyl as defined herein, is dissolved in 20 milliliters of a 1:1 mixture of absolute ethanol and dry benzene. To this solution is added 0.77 grams of hydroxylamine hydrochloride in 15 milliliters of absolute ethanol and 1.12 grams of any organic tertiary amine, such as triethylamine, which is preferred. The solution is heated to reflux and the water formed in the reaction is azeotroped off. After refluxing for 18 hours, the solvent is removed in vacuo, the residue is dissolved in chloroform, extracted with water and saturated sodium chloride solution, and dried over anhydrous magnesium sulfate. Filtration and evaporation affords the crude product oximes of general Formula III where R is alkyl.

c. Procedure for Forming Carboxylate

The appropriate oxime of general Formula III, prepared as above, (0.004 mole) is dissolved in four milliliters of an alkanol of up to four carbon atoms and is added to an alkoxide solution (0.0045 mole of sodium). To this solution is added 0.0045 mole of the appropriate α-halo-substituted carboxylate compound where the halo is chlorine, bromine, or iodine, preferably bromine, and the reaction is followed by thin layer chromatography. The solution can be heated at reflux, if the reaction is sluggish. The product of general Formula I is obtained either by filtration of the product, or by evaporation of the solvent, and dissolving the residue in chloroform, extracting with water, drying and then evaporating the chloroform solvent.

Sodium hydride can be used in place of the sodium alkoxide, and the solvent can be an ether such as tetrahydrofuran, or diethyl ether, etc.

The compounds where R is hydrogen, such as 5-(2-chloro-4-trifluoromethylphenoxy)-2-nitroacetophenone oxime-O-acetic acid, are prepared by simple hydrolysis of the esters, followed by acidification and extraction or filtration of the product.

The compounds where R is an agronomically soluble salt, as defined herein, are made by reacting the appropriate acid with the appropriate base.

B. EXAMPLES

The following examples illustrate the synthesis of compounds of general Formula I by the general procedure described above.

EXAMPLE I

Synthesis of 5-(2-chloro-4-trifluoromethylphenoxy)-2-nitroacetophenone oxime-O-(acetic acid, methyl ester)

a. Preparation of 3-(2-chloro-4-trifluoromethylphenoxy)acetophenone

To a 250 milliliter flask containing a solution of 13.92 grams of the potassium salt of 3-hydroxyacetophenone in 30 milliliters of dry dimethylsulfoxide (DMSO), was added 17.12 grams (0.08 mole) of 3,4-dichlorobenzotrifluoride. The reaction solution was heated to 175° C. for six hours, and then cooled and stirred at ambient temperature for 18 hours. The bulk of the DMSO was removed in vacuo, and the remaining dark residue was stirred with diethyl ether for 15 minutes and filtered. The filtrate was extracted once with water, once with 1 N sodium hydroxide, once with a saturated sodium chloride solution, dried over anhydrous MgSO$_4$, filtered, decolorized with charcoal, and evaporated to dryness leaving 16.04 grams of dark red oil comprised of 3-(2-chloro-4-trifluoromethylphenoxy)acetophenone. The material was further purified by passing through a neutral, grade III alumina column.

b. Nitration of 3-(2-chloro-4-trifluoromethylphenoxy)acetophenone

To a 100 milliliter flask containing a solution of 26 milliliters of concentrated sulfuric acid (H$_2$SO$_4$), and 16 milliliters of ethylenedichloride (EDC), which was cooled to 0° C., 6.28 grams, (0.02 mole) of the dark red oil of 3-(2-chloro-4-trifluoromethylphenoxy)acetophenone (prepared above) was added dropwise to form a brownish-black solution. When the addition of 3-(2-chloro-4-trifluoromethylphenoxy)acetophenone was completed, dry potassium nitrate (KNO$_3$), (2.0 grams, 0.020 mole) was added in small portions over a 20 minute period so as to maintain the reaction mixture below 4° C. The reaction mixture was stirred for 0.5 hours at 0° C. It was then poured into 250 milliliters of ice and water, and the resulting mixture was mixed with 200 milliliters of chloroform, (CHCl$_3$). The organic layer was separated, and then extracted twice with water, once with a saturated sodium chloride solution, and then dried over anhydrous magnesium sulfate, and then filtered. The organic solvent was evaporated off to yield 6.51 grams of an orange oil which analysis showed was a mixture of two positional isomers, one of which was 5-(2-chloro-4-trifluoromethylphenoxy)-2-nitroacetophenone. The mixture was separated into two fractions by high pressure liquid chromatography (HPLC) using diethyl ether as the eluant.

The diethylether was stripped from fraction #1, leaving 2.37 grams of an orange oil comprised of 5-(2-chloro-4-trifluoromethylphenoxy)-2-nitroacetophenone which had the following:

Nuclear magnetic resonance [(NMR) (CDCl$_3$)]: 2.47δ (singlet, 3H); 6.78–8.21δ (multiplet, 6H).

Infra Red (IR): 1710, 1575, 1520, 1400, 1315 cm$^{-1}$.

Mass Spectra (MS) molecular ion at m/e 359.

c. Synthesis of 5-(2-chloro-4-trifluoromethylphenoxy)-2-nitroacetophenone oxime A 100 milliliter flask was charged with a solution of 2.0 grams (0.0056 mole) of the orange oil, 5-(2-chloro-4-trifluoromethylphenoxy)-2-nitroacetophenone, in 10 milliliters of absolute ethanol and 10 milliliters of dry benzene. A solution of hydroxylamie hydrochloride (0.77 grams, 0.011 mole) in 15 milliliters of absolute ethanol was added followed by addition of 1.12 grams (0.011 mole) of an acid acceptor (triethylamine). The reaction mixture was then refluxed; when 20 milliliters of solvent was distilled off, an additional 15 milliliters of benzene was added. Refluxing was continued until 15 milliliters of solvent distilled off, and then the remaining solution was refluxed for 16 hours, with the formation of a mixture of the syn and anti isomers of 5-(2-chloro-4-trifluoromethylphenoxy)-2-nitroacetophenone oxime. The solvent was stripped from the mixture, and the residue was dissolved in chloroform. The chloroform solution was extracted twice with water, then with a saturated solution of sodium chloride, and then dried over anhydrous magnesium sulfate.

The chloroform solution was filtered and the solvent (chloroform) was evaporated to yield 2.03 grams of an orange oil comprised of 5-(2-chloro-4-trifluoromethylphenoxy)-2-nitroacetophenone oxime (anti and syn), which had the following:

Mass spectra (MS): molecular ion at m/e 374

(Syn and Anti) NMR (CDCl$_3$): 2.13δ (singlet, 3H), 6.91–8.17δ (multiplet, 6H): 9.33δ (singlet, 1H).

(Syn and Anti) IR: 3100 (broad), 1605, 1575, 1520, 1400 cm$^{-1}$.

d. Formation of the Syn and Anti Isomers of 5-(2-chloro-4-trifluoromethylphenoxy)-2-nitroacetophenone oxime-O-(acetic acid, methyl ester)

A solution of 0.10 grams (0.0045 milliliters) of sodium metal in 5 milliliters of methanol under nitrogen was charged into a 25 milliliter flask. When all of the sodium had reacted, 1.50 grams (0.004 mole) of the 5-(2-chloro-4-trifluoromethylphenoxy)-2-nitroacetophenone oxime (anti and syn) (prepared above) dissolved in 5 milliliters of methanol was added, and the solution stirred. Methylbromoacetate (0.68 grams, 0.0045 mole) was added to the solution; the resulting mixture was stirred at ambient temperature under nitrogen for eighteen (18) hours, and was then refluxed for two hours. The solvent was stripped from the solution and the residue was dissolved in chloroform (CHCl$_3$). The CHCl$_3$ solution was extracted twice with water, once with a saturated sodium chloride solution, and dried over anhydrous magnesium sulfate. The CHCl$_3$ solution was filtered, and the solvent removed by evaporation to yield 1.68 grams of an orange oil containing the isomers of 5-(2-chloro-4-trifluoromethylphenoxy)-2-nitroacetophenone oxime-O-(acetic acid, methyl ester). The orange oil was purified by chromatography by dissolving it into 3 milliliters of ethyl ether and placing it on top of a seven inch by 21 millimeter column of grade III alumina. The column was eluted with diethyl ether and the desired fractions were collected. The solvent was removed to yield 0.72 grams of a yellow oil comprised of anti and syn isomers of 5-(2-chloro-4-trifluoromethylphenoxy)-2-nitroacetophenone oxime-O-(acetic acid, methyl ester), which had the following:

MS: Molecular ion at m/e 446

Syn and Anti IR: 1760, 1605, 1575, 1520, 1320 cm$^{-1}$.
Syn and Anti NMR (CDCl$_3$): 2.23$\delta$ (singlet, 3H), 3.67$\delta$ and 3.72$\delta$ (singlet, 3H), 4.47$\delta$ and 4.67$\delta$ (singlet, 2H), 6.78–8.25$\delta$ (multiplet, 6H).

Upon dissolving the yellow oil in ethanol (or methanol), pale yellow crystals were obtained with a melting point of 89°–92° C.

EXAMPLE II

Synthesis of the Anti and Syn Isomers of 5-(2-chloro-4-trifluoromethylphenoxy)-2-nitroacetophenone oxime-O-(acetic acid, ethyl ester)

A solution of 0.14 grams (0.0060 mole) of sodium metal in 8 milliliters of methanol under nitrogen gas was charged into a 50 milliliter flask. When all of the sodium had reacted, 2.0 grams (0.0053 mole) of the orange oil, anti and syn isomers of 5-(2-chloro-4-trifluoromethylphenoxy)-2-nitroacetophenone oxime (prepared as in Example Ic) were added, and the solution was stirred. Ethyl-2-bromopropionate (1.06 grams, 0.0059 mole) were added to the solution and resulting mixture was stirred at ambient temperature under nitrogen gas for fifty-one (51) hours. The solvent was stripped from the solution, and the oil residue was stirred in diethyl ether, filtered, and washed well with diethyl ether. The filtrate was washed twice with water, once with a saturated sodium chloride solution, and dried over anhydrous magnesium sulfate. The diethyl ether solution was then filtered, and the solvent removed by evaporation to yield 2.23 grams of an orange oil containing the anti and syn isomers of 5-(2-chloro-4-trifluoromethylphenoxy)-2-nitroacetophenone oxime-O-(acetic acid, ethyl ester). The orange oil was purified by chromatography by dissolving it in diethylether and adding it to the top of an eight inch by 21 millimeter column of neutral grade III alumina. The column was eluted with diethylether and the first component to come off the column was the desired product. The solvent was removed to yield 1.13 grams of a yellow oil comprised of anti and syn isomers of 5-(2-chloro-4-trifluoromethylphenoxy)-2-nitroacetophenone oxime-O-(acetic acid, ethyl ester).

EXAMPLE III

Synthesis of 5-(2-chloro-4-trifluoromethylphenoxy)-2-chlorobenzaldoxime-O-(acetic acid, methyl ester)

a. Preparation of 3-(2-chloro-4-trifluoromethylphenoxy)benzaldehyde dimethyl acetal To a solution of 80.7 grams (0.39 mole) of the potassium (K+) salt of 3-hydroxybenzaldehyde dimethyl acetal in 170 milliliters of dry DMSO was added 77.04 grams (0.36 mole) of 3,4-dichlorobenzotrifluoride. The solution was heated in an oil bath of 150°–155° for four hours and then stirred overnight at ambient temperature.

The solvent was then stripped in vacuo and the residue stirred with CHCl$_3$ and filtered. The filtrate was washed with H$_2$O, 0.5 N NaOH and saturated NaCl solution and dried over anhydrous MgSO$_4$. Filtration and decolorization with charcoal and evaporation of solvent afforded 114.8 grams of a light orange oil comprised of 3-(2-chloro-4-trifluoromethylphenoxy)benzaldehyde dimethyl acetal.

b. Preparation of 5-(2-chloro-4-trifluoromethylphenoxy)-2-chlorobenzaldehyde A 200 milliliter (ml) three-necked flask was charged with ten (10.0) grams (0.029 mole) of the above-mentioned 3-(2-chloro-4-trifluoromethylphenoxy)benzaldehyde dimethyl acetal and 90 milliliters of dry ethylene dichloride. The solution was cooled in an ice bath, and then a catalytic amount (approximately 0.2 grams) of ferric chloride was added to the solution. Chlorine gas addition was started at a moderate rate and continued for one (1) hour at 0° C., and then the solution was stirred for an additional two (2) hours at 0° C. The reaction solution was then purged with nitrogen overnight at ambient temperature.

It was then extracted with water (H$_2$O) and the H$_2$O layer extracted with chloroform (CHCl$_3$). The organic layers of ethylene dichloride and chloroform were combined and again washed with H$_2$O (the H$_2$O being brought to pH 6 with 1 N NaOH). The organic layer was then washed with saturated NaCl solution and dried over anhydrous MgSO$_4$. Filtration and evaporation afforded 11.74 grams of a pale yellow oil comprised of 5-(2-chloro-4-trifluoromethylphenoxy)-2-chlorobenzaldehyde, which had the following NMR, IR, ad MS:

NMR: (CDCl$_3$) 6.87–7.60$\delta$ (multiplet, 6H), 10.37$\delta$ (singlet, 1H).

IR: 1695, 1605, 1590, 1500, 1415, 1320 cm$^{-1}$.

MS: Molecular ion at m/e 334.

c. Preparation of 5-(2-chloro-4-trifluoromethylphenoxy)-2-chlorobenzaldoxime A 100 milliliter flask was charged with 3.34 grams (0.01 mole) of the prepared 5-(2-chloro-4-trifluoromethylphenoxy)-2-chlorobenzaldehyde, 20 milliliters of tetrahydrofuran (THF) and 12 mililiters of absolute ethanol. To this solution was added 0.83 grams (0.012 mole) of hydroxylamine hydrochloride in ten (10) milliliters of water, and then 0.60 grams (0.015 mole) of NaOH in five (5) milliliters of H$_2$O. After stirring the solution at ambient temperature for approximately eighteen (18) hours, the solution was stripped (in vacuo) of the organic solvent and the aqueous residue taken up in a mixture of H$_2$O/CHCl$_3$. The organic layer was phase separated, washed with saturated NaCl solution and dried over anhydrous MgSO$_4$.

Filtration and evaporation afforded 3.01 grams of a beige solid. This material was recrystallized in 40 milliliters of hexane, affording 1.24 grams of beige crystals comprised of 5-(2-chloro-4-trifluoromethylphenoxy)-2-chlorobenzaldoxime (anti and syn) which had an m.p. of 109°–112° C. and the following NMR and IR:

NMR: (CDCl$_3$) 6.83–7.70$\delta$ (multiplet, 6H), 8.45$\delta$ (singlet, 1H), 8.97$\delta$ (singlet, 1H).

IR: 3340–3110, 1605, 1590, 1570, 1485, 1400, 1320 cm$^{-1}$.

d. Preparation of 5-(2-chloro-4-trifluoromethylphenoxy)-2-chlorobenzaldoxime-O-(acetic acid, methyl ester)

A 25 milliliter flask was flushed with dry nitrogen (N$_2$) and then charged with 0.09 grams (0.0037 mole) of sodium and 5 milliliters of dry methanol. When all of the sodium had reacted, 1.24 grams (0.00355 mole) of the 5-(2-chloro-4-trifluoromethylphenoxy)-2-chlorobenzaldoxime in 4 milliliters of methanol was added. After stirring for 15 minutes, 0.57 grams (0.0037 mole) of methyl bromoacetate was added and the solution was stirred overnight (under dry nitrogen) at ambient temperature.

Solvent was then removed in vacuo, the residue dissolved in $CHCl_3$, and extracted with water and saturated NaCl solution and dried over anhydrous $MgSO_4$. Filtration and evaporation of the solvent afforded 1.53 grams of a pale yellow oil. This was dissolved in 2 milliliters of $CHCl_3$ and added to the top of a silica gel-60 column (35 gram, 70–230 mesh, activity 2–3) and eluted with $CHCl_3$. The eluant was collected in 10 milliter fractions and analyzed by thin layer chromatography (TLC). Evaporation of the appropriate fractions (of the first component off the column) afforded 1.02 grams of a clear, colorless oil comprised of 5-(2-chloro-4-trifluoromethylphenoxy)-2-chlorobenzaldoxime-O-(acetic acid, methyl ester), which had the following:

NMR: ($CDCl_3$) 3.75$\delta$ (singlet, 3H); 4.71$\delta$ (singlet, 2H); multiplet centered at 7.31$\delta$ (6H); 8.56$\delta$ (singlet, 1H).

IR: 1760, 1740, 1595, 1565, 1500, 1465, 1320 $cm^{-1}$.

MS: Molecular ion at m/e 421.

EXAMPLE IV

Synthesis of 5-(2-chloro-4-trifluoromethylphenoxy)-2-chlorobenzaldoxime-O-(2-propionic acid, methyl ester)

A 25 milliliter flask was flushed with dry nitrogen ($N_2$) and charged with 6 milliliters of dry MeOH and 0.15 grams (0.0065 mole) of sodium. When all of the sodium had reacted, 2.09 grams (0.006 mole) of the 5-(2-chloro-4-trifluoromethylphenoxy)-2-chlorobenzaldoxime (prepared as in Example Ia.) in 6 milliliters of MeOH was added in one portion and stirred for approximately fifteen (15) minutes at ambient temperature.

To this solution was added 1.12 grams (0.0062 mole) of ethyl-2-bromopropionate in one portion. The resulting solution was stirred at ambient temperature under dry nitrogen overnight.

Solvent was then stripped and the residue dissolved in $CHCl_3/H_2O$, phase separated and the $CHCl_3$ layer extracted with saturated NaCl solution and dried over anhydrous $MgSO_4$. Filtration and evaporation of solvent left 3.0 grams of a crude oil. This was dissolved in 2 milliliters of $CHCl_3$ and applied to the top of a silica gel-60 column (wet-packed with $CHCl_3$) (40 gram, 70–230 mesh, activity 2–3) and eluted with $CHCl_3$. The eluant was collected in 10 milliliter fractions and analyzed by thin layer chromatography (TLC). Evaporation of the appropriate fractions (fractions 6–13) afforded 1.94 grams of a clear, colorless oil comprised of 5-(2-chloro-4-trifluoromethylphenoxy)-2-chlorobenzaldoxime-O-(2-propionic acid, methyl ester), which had the following:

NMR ($CDCl_3$): 1.46$\delta$ (doublet, 3H); 3.67$\delta$ (singlet, 3H); 4.73$\delta$ (quartet, 1H); 7.18$\delta$ (multiplet, 6H); 8.44$\delta$ (singlet, 1H);

IR: 1760, 1610, 1600, 1565, 1500, 1465, 1320 $cm^{-1}$; and

MS: Molecular ion at m/e 435.

The following compounds were prepared by procedures described herein and illustrated by Examples I, II, III, and IV.

EXAMPLE V 5-(2-chloro-4-trifluoromethylphenoxy)-2-nitroacetophenone oxime-O-(2-propionic acid, methyl ester), a yellow oil which had the following:

NMR ($CDCl_3$): 1.29$\delta$ and 1.51$\delta$ (2 doublets, 3H); 2.25$\delta$ (singlet, 3H); 3.69$\delta$ and 3.73$\delta$ (2 singlets, 3H); 4.64$\delta$ and 4.80$\delta$ (2 quartets, 1H); 7.0–8.25 $\delta$ (multiplets, 6H).

IR: 1750, 1575, 1525, 1315 $cm^{-1}$; and

MS: Molecular ion at at m/e 460.

EXAMPLE VI 5-(2-chloro-4-trifluoromethylphenoxy)-2-nitroacetophenone oxime-O-acetic acid, a yellow oil prepared by saponification of methyl ester, which had the following:

NMR ($CDCl_3$): 2.19$\delta$ (singlet, 3H); 4.50$\delta$ and 4.17$\delta$ (singlets, 2H); 6.93–8.24$\delta$ (multiplet, 6H); 10.92$\delta$ (singlet, 1H); and IR: 3000–3400 (broad), 1730, 1575, 1525, 1315 $cm^{-1}$.

EXAMPLE VII 5-(2-chloro-4-trifluoromethylphenoxy)-2-nitrobenzaldoxime, a viscous semi-solid with the following:

NMR ($CDCl_3$): 6.93–8.13$\delta$ (multiplet, 6H); 8.13$\delta$ (singlet, 1H); 9.49$\delta$ (broad singlet, 1H);

IR: 3310 (broad), 1605, 1570, 1520, 1490, 1400, 1315 $cm^{-1}$; and

MS: Molecular ion at m/e 360.

EXAMPLE VIII 5-(2-chloro-4-trifluoromethylphenoxy)-2-nitrobenzaldoxime-O-(acetic acid, methyl ester), when recrystallized from MeOH, gave a pale yellow solid (m.p. 72°–76°) which had the following:

NMR ($CDCl_3$): 3.76$\delta$ (singlet, 3H); 4.72$\delta$ (singlet, 2H); 6.93–7.79$\delta$ (multiplet, 5H); 8.13$\delta$ (doublet, 1H); 8.78$\delta$ (singlet, 1H);

IR: 1755, 1600, 1565, 1515, 1315 $cm^{-1}$; and

MS: Molecular ion at m/e 432.

EXAMPLE IX 5-(2-chloro-4-trifluoromethylphenoxy)-2-nitrobenzaldoxime-O-(2-propionic acid, methyl ester), a pale yellow liquid with the following:

NMR ($CDCl_3$): 1.52$\delta$ (doublet, 3H); 3.72$\delta$ (singlet, 3H); 4.84$\delta$ (quartet, 1H); multiplet centered at 7.35$\delta$ (5H), 8.12$\delta$ (doublet, 1H), 8.75$\delta$ (singlet, 1H);

IR: 1750, 1605, 1565, 1520, 1315 $cm^{-1}$;

MS: Molecular ion at m/e 446.

EXAMPLE X 5-(2-chloro-4-trifluoromethylphenoxy)-2-nitrobenzaldoxime-O-(acetic acid, isopropyl ester), a yellow crystalline solid with the following:

NMR ($CDCl_3$): 1.23$\delta$ (doublet, 6H); 4.63$\delta$ (singlet, 2H); 5.06$\delta$ (heptet, 1H); multiplet centered at 7.33$\delta$ (5H); 8.09$\delta$ (doublet, 1H), 8.63$\delta$ (singlet, 1H);

IR: 2980, 2940, 1750, 1605, 1570, 1520, 1315 $cm^{-1}$; and

MS: Molecular ion at m/e 460.

Applications of the Compositions Against Weeds

The novel compounds of this invention are particularly valuable for preemergence and postemergence weed control because they are toxic to many species and groups of weeds and are relatively nontoxic to many beneficial plants. The exact amount required of one or more of the compounds described herein depends upon a variety of factors, including the hardiness of the particular weed species, the weather, the type of soil, the method of application, the kind of beneficial plants in the same area, and the like. Thus, while the application of up to only about 0.1 pounds of active compound per acre may be sufficient for good control of a light infestation of weeds growing under adverse conditions, the application of 2 pounds or more of an active compound per acre may be required for good control of a dense infestation of hardy perennial weeds growing under favorable conditions. The preferred compounds mentioned herein are generally used at the lower application rates such as from 0.1 to 10 pounds per acre; the less preferred but generally useful compounds are generally applied at the higher applications of from 10 to 20 pounds per acre, and those compounds which are intermediate between the most preferred compounds and the generally useful compounds are generally applied at rates from 5 to 15 pounds per acre.

a. Examples Of Weeds Which May Be Controlled By The Compounds Described Herein

Weeds are undesirable plants growing where they are not wanted and may be classified as broadleaf or grassy weeds, a classification which includes many types of known weeds. Many weeds are controlled by the compositions set forth herein, when applied in a herbicidally effective amount. These include:

| | |
|---|---|
| Aster spp., e.g. | |
| Aster spinosus Benth. | (aster, spiny) |
| Aster simplex Willd. | (aster, white field) |
| Aster parryi Gray | (aster, woody) |
| Hordeum leporinum Link | (barley, wild) |
| Galium spp., e.g. | |
| Galium aparine L. | (bedstraw, catchweed) |
| Galium asprellum Michx. | (bedstraw, rough) |
| Galium verum L. | (bedstraw, yellow) |
| Cynodon dactylon (L.) Pers. | (bermudagrass) |
| Convolvulus arvensis L. | (bindweed, field) |
| Convolvulus sepium L. | (bindweed, hedge) |
| Fagopyrum tataricum (L.) Gaertn. | (buckwheat, Tartary) |
| Scirpus spp., e.g. | |
| Scirpus atrovirens Willd. | (bulrush, green) |
| Scirpus fluviatilis (Torr.) Gray | (bulrush, river) |
| Arctium spp., e.g. | |
| Arctium minus (Hill) Bernh. | (burdock, common) |
| Mollugo verticillata L. | (carpetweed) |
| Daucus carota L. | (carrot, wild) |
| Silene cserei Baumg. | (campion, biennial) |
| Silene cucubalus Wibel | (campion, bladder) |
| Lychnis floscuculi L. | (campion, meadow) |
| Lychnis dioica L. | (campion, red) |
| Typha spp., e.g. | |
| Typha latifolia L. | (cattail, common) |
| Anthemis spp., e.g. | |
| Anthemis arvensis L. | (chamomile, corn) |
| Bromus spp., e.g. | |
| Bromus secalinus L. | (cheat) |
| Bromus tectorum L. | (downy brome) |
| Stellaria media (L.) Cyrillo | (chickweed, common) |
| Cerastium spp., e.g. | |
| Cerastium vulgatum L. | (chickweed, mouseear) |
| Agrostemma githago L. | (cockle, corn) |
| Saponaria vaccaria L. | (cockle, cow) |
| Lychnis alba Mill. | (cockle, white) |
| Croton spp., e.g. | |
| Croton gladulosus L. | (croton, tropic) |
| Cuphea petiolata (L.) Kochne | (cuphea, clammy) |
| Cuphea carthagenensis (Jacq.) McBride | (cuphea, tarweed) |
| Taraxacum spp., e.g. | |
| Taraxacum officinale Weber | (dandelion, common) |
| Rumex spp., e.g. | |
| Rumex crispus L. | (dock, curly) |
| Rumex acetosa L. | (sorrel) |
| Cuscuta spp., e.g. | |
| Cuscuta indecora Choisy | (dodder, largeseed) |
| Cuscuta planiflora Tenore | (dodder, smallseed) |
| Eupatorium capillifolium (Lam.) | (dogfennel) |
| Heteranthera limosa (Sw.) Willd. | (ducksalad) |
| Krigia virginica (L.) Willd. | (dwarfdandelion, Virginia) |
| Emex australis Steinh. | (emex) |
| Emex spinosa Campd. | (emex, spiny) |
| Pyrrhopappus carolinianus (Walt.) D.C. | (falsedandelion, Carolina) |
| Fumaria officinalis L. | (fumitory) |
| Eleusine indica (L.) Gaertn. | (goosegrass) |
| Lithospermum spp., e.g. | |
| Lithospermum officinale L. | (gromwell, common) |
| Senecio spp., e.g. | |
| Senecio vulgaris L. | (groundsel, common) |
| Galeopsis tetrahit L. | (hempnettle) |
| Solanum spp., e.g. | |
| Solanum carolinense L. | (horsenettle) |
| Equisetum spp., e.g. | |
| Equisetum arvense L. | (horsetail, field) |
| Cynoglossum officinale L. | (houndstongue) |
| Vernonia spp., e.g. | |
| Vernonia altissima Nutt. | (ironweed, tall) |
| Centaurea spp., e.g. | |
| Centaurea repens L. | (knapweed, Russian) |
| Centaurea maculosa Lam. | (knapweed, spotted) |
| Scleranthus annuus L. | (knawel) |
| Polygonum, spp., e.g. | |
| Polygonum aviculare L. | (knotweed, prostrate) |
| Polygonum convolvulus L. | (buckwheat, wild) |
| Polygonum pensylvanicum L. | (smartweed, Pennsylvania) |
| Kochia scoparia (L.) Schrad. | (kochia) |
| Modiola caroliniana (L.) G. Don | (mallow, bristly) |
| Malva spp., e.g. | |
| Malva neglecta Wallr. | (mallow, common) |
| Hibiscus trionum L. | (mallow, Venice) |
| Medicago lupulina L. | (medic, black) |
| Panicum obtusum H.B.K. | (mesquite, vine) |
| Asclepias spp., e.g. | |
| Asclepias syriaca L. | (milkweed, common) |
| Asclepias verticillata L. | (milkweed, western whorled) |
| Sarcostemma cyanchoides Dcne. | (milkweed, climbing) |
| Ampelamus albidus (Nutt.) Britt. | (milkweed, honeyvine) |
| Verbascum spp., e.g. | |
| Verbascum thapsus L. | (mullein, common) |
| Najas spp., e.g. | |
| Najas marina L. | (naiad, hollyleaf) |
| Cyperus strigosus L. | (nutsedge, false) |
| Cyperus rotundus L. | (nutsedge, purple) |
| Cyperus esculentus L. | (nutsedge, yellow) |
| Panicum spp., e.g. | |
| Panicum dichotomiflorum Michx. | (panicum, fall) |
| Panicum texanum Buckl. | (panicum, Texas) |
| Thlaspi arvense L. | (pennycress, field) |
| Thlaspi perfoliatum L. | (pennycress, thoroughwort) |
| Potamogeton spp., e.g. | |
| Potamogeton nodosus Poir. | (pondweed, American) |
| Portulaca oleracea L. | (purslane, common) |
| Richardia scabra L. | (purslane, Florida) |
| Agropyron repens (L.) Beauv. | (quackgrass) |
| Ambrosia spp., e.g. | |
| Ambrosia artemisiifolia L. | (ragweed, common) |
| Ambrosia trifida L. | (ragweed, giant) |
| Ambrosia psilostachya D.C. | (ragweed, western) |
| Echinochloa colonum (L.) Link | (jungle-rice) |
| Oryza sativa L. | (rice, red) |
| Lolium multiflorum Lam. | (ryegrass, Italian) |
| Sesbania vesicaria (Jacq.) Ell. | (sesbania, bagpod) |
| Sesbania exaltata (Raf.) Cory | (sesbania, hemp) |
| Cassia obtusifolia L. | (sicklepod) |
| Leptochloa uninervia (presl) Hitchc. & Chase | (sprangletop, Mexican) |
| Leptochloa filiformis (Lam.) Beauv. | (sprangletop, red) |
| Euphorbia spp., e.g. | |
| Euphorbia cyparissias L. | (spurge, cypress) |
| Euphorbia supina Raf. | (spurge, prostrate) |

| | |
|---|---|
| *Euphorbia maculata* L. | (spurge, spotted) |
| *Panicum virgatum* L. | (switchgrass) |
| *Spergula arvensis* L. | (spurry, corn) |
| *Cnicus benedictus* L. | (thistle, blessed) |
| *Echium vulgare* L. | (thistle, blue) |
| *Cirsium* spp., e.g. | |
| *Cirsium vulgare* (Savi) Tenore | (thistle, bull) |
| *Cirsium arvense* (L.) Scop. | (thistle, Canada) |
| *Carduus nutans* L. | (thistle, musk) |
| *Salsola kali* L. var. *tenuifolia* Tausch | (thistle, Russian) |
| *Linaria* spp., e.g. | |
| *Linaria vulgaris* Hill | (toadflax, yellow) |
| *Hydrochloa caroliniensis* Beauv. | (watergrass, southern) |
| *Barbarea verna* (mill.) Aschers | (wintercress, early) |
| *Panicum capillare* L. | (witchgrass) |
| *Achillea millefolium* L. | (yarrow, common) |
| *Achillea lanulosa* Nutt. | (yarrow, western) |

The compounds of the invention, particularly the preferred compounds, for example, 5-(2-chloro-4-trifluoromethylphenoxy)-2-chlorobenzaldoxime-O-(2-propionic acid, methyl ester), when applied postemergence at rates as low as one (1) pound per acre (1.1 kilograms per hectare) or less are very effective against weeds of the genera: Sida, Datura, Brassica, Setaria, Sorghum, Sesbania, Abutilon, Ipomoea, Avena, and Echinochloa.

The compounds of the invention, particularly the preferred compounds, for example, 5-(2-chloro-4-trifluoromethylphenoxy)-2-chlorobenzaldoxime-O-(2-propionic acid, methyl ester), when applied postemergence at rates as low as one (1) pound per acre (1.1 kilograms per hectare) are very effective against the weed species: *Sida spinosa* (L) (teaweed), *Datura stramonium* (L) (jimsonweed), *Brassica kaber* (D.C.) (wild mustard), *Setaria glauca* (L) (yellow foxtail), *Digitaria sanguinalis* (L) (large crabgrass), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Avena fatua* (L) (wild oats), *Echinochloa crusgalli* (L) (barnyardgrass), and *Gossypium hirsutum* (L) (cotton as a weed).

The compounds of the invention, particularly the preferred compounds, for example, 5-(2-chloro-4-trifluoromethylphenoxy)-2-chlorobenzaldoxime-O-(2-propionic, methyl ester), are safe to crops of corn, wheat, and rice, when applied postemergence at rates of one (1) pound per acre (1.1 kilograms per hectare) or less. Others are also safe to soybeans.

The compounds of the invention, particularly the preferred compounds, for example, 5-(2-chloro-4-trifluoromethylphenoxy)-2-nitroacetophenone oxime-O-acetic acid, when applied preemergence at rates as low as one-half (0.5) pound per acre (0.55 kilograms per hectare) are very effective against weeds of the genera: Sida, Datura, Brassica, Setaria, Digitaria, Sorghum, Sesbania, Abutilon, Ipomoea, Avena, and Echinochloa.

The compounds of the invention, particularly the preferred compounds, for example, 5-(2-chloro-4-trifluoromethylphenoxy)-2-nitroacetophenone oxime-O-acetic acid, when applied preemergence at rates as low as one-half (0.5) pounds per acre (0.55 kilograms per hectare) are very effective against the weed species: *Sida spinosa* (L) (teaweed), *Datura stramonium* (L) (jimsonweed), *Brassica kaber* (D.C.) (wild mustard), *Setaria glauca* (L) (yellow foxtail), *Digitaria sanguinalis* (L) (large crabgrass), *Sorghum halepense* (L) (johnsongrass), *Sesbania* spp. (L) (coffeeweed), *Abutilon theophrasti* (l) (velvetleaf), *Ipomoea purpurea* (L) Roth (tall morningglory), *Avena fatua* (L) (wild oats), *Echinochloa crusgalli* (L) (barnyardgrass), and *Gossypium hirsutum* (L) (cotton as a weed).

The compounds of the invention, particularly the preferred compounds, for example 5-(2-chloro-4-trifluoromethylphenoxy)-2-nitroacetophenone oxime-O-acetic acid, are safe to crops of cotton, corn, and soybeans when applied preemergence at rates of one-half (0.5) pounds per acre (0.5 kilograms per hectare). Other compounds as described herein are safe on wheat and rice, as well as corn and cotton.

b. Description Of The Method Of Controlling Weeds

As used herein and in the claims, the method of controlling the weeds comprises contacting the weeds with a herbicidally effective amount of a composition represented by Formula I described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, but preferably after they emerge with one or more of the compounds represented by Formula I described herein. The phrase "the herbicidally effective amount" refers to that amount required under the environmental conditions in order to effectively control, that is, the weeds are severely injured so as not to be able to recover from the application of the compound or are killed. The phrase "a safe amount" refers to that amount under environmental conditions which cause no substantial injury to the crops.

c. Other Uses

The compounds of the invention may also be used as a dessicant, defoliant, dehiscent, or growth regulant, for examples, potatoe vine dessicant, cotton defoliant as well as dehiscent, or as a growth regulant for brush growth control.

d. General Application Of The Compounds

For practical use as herbicides or other pesticidal use, the compounds of this invention are generally incorporated into herbicidal and/or pesticidal formulations which comprise an "inert carrier and a herbicidally and/or pesticidally toxic amount of one or more of the compounds mentioned herein". Such formulations enable the active compound to be applied conveniently to the appropriate site in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculities, usually of a particle size range of from about 0.3 to 1.5 millimeters. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestations.

A typical herbicidal formulation according to this invention is illustrated by the following example, in which the quantities are in parts by weight.

EXAMPLE XI

Preparation of a Dust

| Product of Example I | 10 |
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Use Of Compounds Alone Or In Mixtures

Although all of the compounds described herein and represented by Formula I described herein are useful as herbicides, some of these are preferred and are better for applications against weeds. In general, all of the compounds described herein may be used either alone or together in mixtures of the compounds described herein. When used in mixtures, the amount or ratio of one compound to another may vary from 0.01 to 100. The amount to use ranges from 0.10 pounds per acre to 2 pounds or more per acre depending upon the conditions.

e. Manner Of Application Of The Compounds Of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulation and the purpose for which it is designed; but generally the herbicidal formulations will comprise from about 0.05 to about 95 percent by weight of the active compounds of this invention. In a preferred embodiment of this invention, the herbicidal formulations will comprise from about 5 to 75 percent by weight of the active compound. The formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples Of Other Pesticides And Herbicides For Combinations

The other herbicides, defoliants, desiccants, and plant growth inhibitors, with which the compounds of this invention can be used in the herbicidal formulations to control weeds, can include: chlorophenoxy herbicides such as 2,4-D, 2,4,5-T, MCPA, MCPB, 4-(2,4-DB), 2,4-DEB, 4-CPB, 4-CPA, 4-CPP, 2,4,6-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, pebulate, vernolate and the like; substituted urea herbicides such as norea, siduron, dichloroal urea, chloroxuron, cycluron, fenuron, monuron, monuron TCA, diuron, linuron, monolinuron, neburon, buturon, trimeturon, and the like; symmetrical triazine herbicides such as simazine, chlorazine, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloropropionic acid, 2,2,3-TPA, and the like; chlorinated benzoic acid and phenylacetic acid herbicides such as 2,3,6-TBA, 2,3,5,6-TBA, dicamba, tricamba, amiben, fenac, PBA, 2-methoxy-3,5-dichlorophenylacetic acid, 3-methoxy-2,6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazide, phenyl mercuric acetate, endothall, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, dipheratril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular patent compounds.

g. Examples of Herbicidal Control

The following examples illustrate the utility of the compounds described herein, for the control of weeds.

The tests described herein were conducted in a laboratory under laboratory conditions in accordance with standard herbicidal testing procedures for preemergence and postemergence control. The plants are observed for a period of days after treatment, and observations were recorded to determine if the weeds are controlled, that is severely injured so that the plants do not recover, or are killed.

EXAMPLE XII

When 5-(2-chloro-4-trifluoromethylphenoxy)-2-nitroacetophenone oxime-O-(acetic acid, methyl ester) from Example I was applied preemergence at two (2) pounds per acre to the weeds of *Sida spinosa* (L) (teaweed), *Datura stramonium* (L) (jimsonweed), *Brassica kaber* (L) (wild mustard), *Setaria glauca* (L) (yellow foxtail), *Digitaria sanguinalis* (L) (large crabgrass), *Sorghum halepense* (L) (johnsongrass), *Sesbania* spp. (coffeeweed), *Abutilon theophrasti* (L) (velvetleaf), *Ipomoea purpurea* (L) Roth (tall morningglory), *Echinochloa crusgalli* (L) (barnyardgrass), all of the weeds were controlled.

EXAMPLE XIII

When 5-(2-chloro-4-trifluoromethylphenoxy)-2-nitroacetophenone oxime-O-(acetic acid, methyl ester) from Example I was applied postemergence at two (2) pounds per acre to *Sida spinosa* (L) (teaweed), *Datura stramonium* (jimsonweed), *Brassica kaber* (wild mustard), *Setaria glauca* (L) (yellow foxtail), *Gossypium hirsutum* (cotton), *Sesbania* spp. (coffeeweed), *Abutilon theophrasti* (velvetleaf), *Ipomoea purpurea* (L) Roth (tall morningglory), *Sorghum halepense* (johnsongrass), *Avena fatua* (L) (wild oats), and *Echinochloa crusgalli* (L) (barnyardgrass), all the weeds were controlled within 21 days.

EXAMPLE XIV

When the compound 5-(2-chloro-4-trifluoromethylphenoxy)-2-chlorobenzaldoxime-O-(acetic acid, methyl ester) from Example III was applied preemergence at ten (10) pounds per acre (11.1 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), and *Echinochloa crusgalli* (L) (barnyardgrass), all of the weeds were severely injured and many were killed after twenty-three (23) days.

EXAMPLE XV

When the compound 5-(2-chloro-4-trifluoromethylphenoxy)-2-chlorobenzaldoxime-O-(acetic acid, methyl ester) from Example III was applied postemergence at one (1) pound per acre (1.1 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), and *Gossypium hirsutum* (L) (cotton, as a weed), all of the weeds were severely injured and many were killed after twenty-two (22) days.

EXAMPLE XVI

When the compound 5-(2-chloro-4-trifluoromethylphenoxy)-2-chlorobenzaldoxime-O-(2-propionic, methyl ester) from Example IV was applied preemergence at four (4) pounds per acre (4.4 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sesbania* spp. (L) (coffeeweed), *Abutilon theophrasti* (L) (velvetleaf), and *Ipomoea purpurea* (L) Roth (tall morningglory), all of the weeds were severely injured and many were killed after twenty-two (22) days, and it was safe for corn, wheat, and rice.

EXAMPLE XVII

When the compound 5-(2-chloro-4-trifluoromethylphenoxy)-2-chlorobenzaldoxime-O-(2-propionic, methyl ester) from Example IV was applied postemergence at one (1) pound per acre (1.1 kilograms per hectare) against the weeds: *Sida spinosa* (L) (teaweed), *Datura stramonium* (L) (jimsonweed, *Setaria glauca* (L) (yellow foxtail), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Avena fatua* (L) (wild oats), *Echinochloa crusgalli* (L) (barnyardgrass), and *Gossypium hirsutum* (L) (cotton, as a weed), all of the weeds were severely injured and many were killed after twenty-two (22) days, and it was safe for corn, wheat, and rice.

EXAMPLE XVIII

When the compound 5-(2-chloro-4-trifluoromethylphenoxy)-2-nitroacetophenone-O-(2-propionic acid, methyl ester) from Example V was applied preemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Avena fatua* (L) (wild oats), and *Echinochloa crusgalli* (L) (barnyardgrass), all of the weeds were severely injured and many were killed after 20 days.

EXAMPLE XIX

When the compound 5-(2-chloro-4-trifluoromethylphenoxy)-2-nitroacetophenone-O-(2-propionic acid, methyl ester) from Example V was applied postemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Avena fatua* (L) (wild oats), and *Gossypium hirsutum* (L) (cotton, as a weed), all of the weeds were severely injured and many were killed after twenty (20) days.

EXAMPLE XX

When the compound 5-(2-chloro-4-trifluoromethylphenoxy)-2-nitroacetophenone-O-acetic acid from Example VI was applied preemergence at one-half (0.5) pounds per acre (0.55 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Avena fatua* (L) (wild oats), and *Echinochloa crusgalli* (L) (barnyardgrass), all of the weeds were severely injured and many were killed after twenty-one (21) days, and it was safe for cotton, soybeans, and corn.

EXAMPLE XXI

When the compound 5-(2-chloro-4-trifluoromethylphenoxy)-2-nitroacetophenone-O-acetic acid from Example VI was applied postemergence at one-half (0.5) pounds per acre (0.55 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Sesbania* spp. (L) (coffeeweed), *Abutilon theophrasti* (L) (velvetleaf), *Ipomoea purpurea* (L) Roth (tall morningglory), and *Gossypium hirsutum* (L) (cotton, as a weed), all of the weeds were severely injured and many were killed.

EXAMPLE XXII

When the compound 5-(2-chloro-4-trifluoromethylphenoxy)-2-nitrobenzaldoxime-O-(acetic acid, methyl ester) from Example VIII was applied preemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sesbania* spp. (L) (coffeeweed), *Abutilon theophrasti* (L) (velvetleaf), and *Ipomoea purpurea* (L) Roth (tall morningglory), all of the weeds were severely injured and many were killed after twenty-one (21) days, and it was safe on soybeans, corn, and rice.

EXAMPLE XXIII

When the compound 5-(2-chloro-4-trifluoromethylphenoxy)-2-nitrobenzaldoxime-O-(acetic acid, methyl ester) from Example VIII was applied postemergence at one (1) pound per acre (1.1 kilograms per hectare) against the weeds: *Sida spinosa* (L) (teaweed), *Datura stramonium* (1) (jimsonweed), *Brassica kaber* (D.C.) (mustard, wild), *Sorghum halepense* (L) (johnsongrass), *Sesbania* spp. (L) (coffeeweed), *Abutilon theophrasti* (L) (velvetleaf), *Ipomoea purpurea* (L) Roth (tall morningglory), *Echinochloa crusgalli* (L) (barnyardgrass), and *Gossypium hirsutum* (L) (cotton, as a weed), all of the weeds were severely injured and many were killed after twenty-seven (27) days, and it was safe for soybeans and rice.

EXAMPLE XXIV

When the compound 5-(2-chloro-4-trifluoromethylphenoxy)-2-nitrobenzaldoxime-O-(2-propionic acid, methyl ester) from Example IX was applied preemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sesbania* spp. (L) (coffeeweed), *Abutilon theophrasti* (L) (velvetleaf), and *Ipomoea purpurea* (L) Roth (tall morningglory), all of the weeds were severely injured and many were killed after twenty-one (21) days, and many were killed after twenty-one (21) days, and it was safe for corn and rice.

EXAMPLE XXV

When the compound 5-(2-chloro-4-trifluoromethylphenoxy)-2-nitrobenzaldoxime-O-(2-propionic acid, methyl ester) from Example IX was applied postemergence at one-half (0.5) pounds per acre (0.55 kilograms per hectare) against the weeds: *Sida spinosa* (L) (teaweed), *Datura stramonium* (L) (jimsonweed), *Brassica kaber* (D.C.) (mustard, wild), *Sesbania* spp. (L) (coffeeweed), *Abutilon theophrasti* (L) (velvetleaf), *Ipomoea purpurea* (L) Roth (tall morningglory), and *Gossypium hirsutum* (L) (cotton, as a weed), all of the weeds were severely injured and many were killed after twenty-two (22) days, and it was safe for wheat and rice.

EXAMPLE XXVI

When the compound 5-(2-chloro-4-trifluoromethylphenoxy)-2-nitrobenzaldoxime-O-(acetic acid, isopropyl ester) from Example X was applied preemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Setaria glauca* (L) (yellow foxtail), *Digitaria sanguinalis* (L) (large crabgrass), *Sesbania* spp. (L) (coffeeweed), *Abutilon theophrasti* (L) (velvetleaf), and *Ipomoea purpurea* (L) Roth (tall morningglory), all of the weeds were severely injured and many were killed after twenty-two (22) days.

EXAMPLE XXVII

When the compound 5-(2-chloro-4-trifluoromethylphenoxy)-2-nitrobenzaldoxime-O-(acetic acid, isopropyl ester) from Example X was applied postemergence at two (2) pounds per acre (2.2 kilograms per hectare) against the weeds: *Sida spinosa* (L) (teaweed), *Datura stramonium* (L) (jimsonweed), *Brassica kaber* (D.C.) (mustard, wild), *Digitaria sanguinalis* (L) (large crabgrass), *Sesbania* spp. (L) (coffeeweed), *Abutilon theophrasti* (L) (velvetleaf), and *Ipomoea purpurea* (L) Roth (tall, morningglory), all of the weeds were severely injured and many were killed after twenty-two (22) days.

While the invention has been described with reference to specific details of certain illustrative embodiments, it is not intended that it shall be limited thereby except insofar as such details appear in the accompanying claims.

I claim:

1. A compound of Formula III:

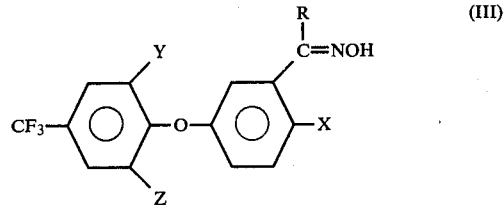

wherein:
X is nitro (—NO$_2$), a halogen, or cyano (—CN);
Y is hydrogen or chlorine;
Z is chlorine when Y is chlorine or Z is hydrogen when Y is chlorine or hydrogen; and
R is hydrogen or an alkyl of up to three carbon atoms.

* * * * *